United States Patent [19]

Magee

[11] Patent Number: 4,461,764
[45] Date of Patent: Jul. 24, 1984

[54] PESTICIDAL PHOSPHORYL- AND PHOSPHINYL-THIOALKYL CYCLIC SUFONES

[75] Inventor: Philip S. Magee, Vallejo, Calif.

[73] Assignee: Chevron Research Company, San Francisco, Calif.

[21] Appl. No.: 421,178

[22] Filed: Sep. 22, 1982

[51] Int. Cl.³ .................. A01N 57/32; C07F 9/24
[52] U.S. Cl. .................. 424/202; 549/6; 549/8
[58] Field of Search .................. 549/6, 8; 424/202

[56] References Cited

U.S. PATENT DOCUMENTS

| | | | |
|---|---|---|---|
| 3,475,452 | 10/1969 | Newallis et al. | 549/8 |
| 3,671,547 | 6/1972 | Stevick | 549/8 |
| 4,128,562 | 12/1978 | Perronnet et al. | 549/8 |
| 4,268,506 | 5/1981 | Baumann et al. | 424/202 |

Primary Examiner—Richard Raymond
Attorney, Agent, or Firm—S. R. LaPaglia; T. G. DeJonghe; S. L. Biggs

[57] ABSTRACT

Compounds of the formula:

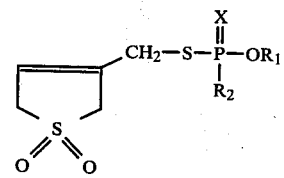

wherein X is sulfur or oxygen; $R_1$ is lower alkyl; $R_2$ is lower alkyl, lower straight chain alkoxy, lower alkylthio, phenyl or the group $-NR_3R_4$ where $R_3$ and $R_4$ are independently hydrogen or lower alkyl, provided that when X is oxygen, $R_2$ is not phenyl, are pesticidal, exhibiting activity against pests such as plant fungal diseases and, in many cases, insects.

9 Claims, No Drawings

PESTICIDAL PHOSPHORYL- AND PHOSPHINYL-THIOALKYL CYCLIC SUFONES

BACKGROUND OF THE INVENTION

This invention relates to certain novel pesticidal phosphoryl- and phosphinyl-thioalkyl-cyclic sulfones and their use as insecticides and fungicides. The compounds of the invention are active as fungicides. Additionally some of the compounds of this invention are active as insecticides.

U.S. Pat. No. 4,268,506 discloses compounds of the formula:

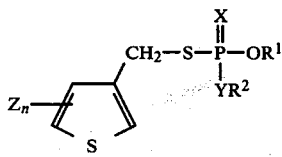

where $R^1$ denotes methyl or ethyl, $R^2$ denotes linear or branded alkyl of a maximum of 5 carbon atoms, X denotes oxygen or sulfur, Y denotes sulfur or —NH—, Z denotes halogen and n denotes one of the integers 0, 1, 2 and 3, which are effective against pests, especially insects, Arachnida and Nemathelminthes.

U.S. Pat. No. 3,563,725 discloses pre-emergent herbicides of the formula:

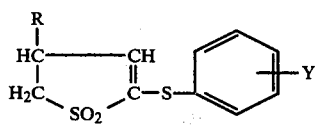

wherein R is either hydrogen, chlorine, or methyl, and Y is hydrogen, an alkyl having 1 to 8 carbon atoms, chlorine or bromine.

SUMMARY OF THE INVENTION

The pesticidal compounds of this invention are represented by the formula:

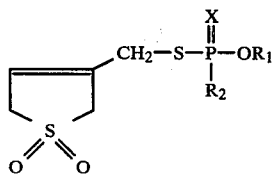

wherein X is sulfur or oxygen; $R_1$ is lower alkyl; $R_2$ is lower alkyl, lower straight-chain alkoxy, lower alkylthio, phenyl or the group $NR_3R_4$ wherein $R_3$ and $R_4$ are independently hydrogen or lower alkyl, provided that when X is oxygen, $R_2$ is not phenyl.

Among other factors, the present invention is based on my finding that these cyclic sulfone compounds are surprisingly active a pesticides, especially as fungicides and insecticides.

Representative $R_1$ groups include methyl and ethyl.

Representative $R_2$ groups include ethyl, ethoxy, methylthio, amino, methylamino and phenyl.

Preferred are the compounds where $R_2$ is lower alkyl, amino or lower alkylamino.

DEFINITIONS

As used herein, the following terms have the following meanings unless expressly stated to the contrary.

The term "alkyl" refers to both straight- and branched-chain alkyl groups. The term "lower alkyl" refers both to straight- and branched-chain alkyl groups having a total of from 1 to 6 carbon atoms and includes primary, secondary and tertiary alkyl groups. Typical lower alkyls include, for example, methyl, ethyl, n-propyl, isopropyl and the like.

The term "alkoxy" refers to the group R'O— wherein R' is alkyl. The term "lower straight-chain alkoxy" refers to alkoxy groups having a straight chain of from 2 to 6 carbon atoms [e.g., —O—(CH$_2$)$_3$CH$_3$]; examples include ethoxy, n-butoxy and the like.

The term "alkylthio" refers to the group —SR' wherein R' is alkyl. The term "lower alkylthio" refers to alkylthio groups having a total of from 1 to about 6 carbon atoms; examples include methylthio, ethylthio, propylthio, and the like.

The term "alkylamino" refers to the group —NR'R" wherein R' is alkyl and R" is hydrogen or alkyl. The term "lower alkylamino" refers to alkylamino groups wherein R' has a total of 1 to 6 carbon atoms and R" has a total of 0 to 6 carbon atoms. Examples include: methylamino, dimethylamino, ethylamino, ethylmethylamino, propylamino and the like.

The term "halo" or "halogen" refers to the groups fluoro, chloro, bromo and iodo.

The term "cyclic sulfone", "sulfolene" or "sulfolenyl" refers to the

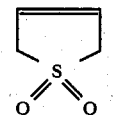

group. The conventional numbering system for this group is shown below.

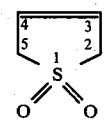

The term "pest" refers to any insect, rodent, nematode, fungus, weed, or any form of terrestrial or aquatic plant or animal life or virus, or bacterial organism or microorganisms (except those viruses, bacteria or other microorganisms existing in living humans or other living animals) considered injurious to health, the environment or man's economic well-being.

The term "pesticide" refers to chemical entities or mixtures thereof intended for preventing, destroying, repelling or mitigating any pest. Thus, the term "pesticide" includes inter alia insecticides, rodenticides, nematocides, molluscicides, bactericides, fungicides, herbicides, algicides and the like.

The terms "insecticide" and "insect" as used herein refer to their broad and commonly understood usages rather than to those creatures which, in the strict biological sense, are classified as insects. Thus, the term "insect" is used not only to include small invertebrate animals belonging to the class "Insecta", but also refers to other related classes of arthropods, whose members are segmented invertebrates having more or fewer than six legs such as spiders, mites, ticks, centipedes, worms and the like.

DETAILED DESCRIPTION OF THE INVENTION

The compounds of this invention may be prepared by phosphorylation of the appropriate 3-halomethyl cyclic sulfone according to the following reaction scheme:

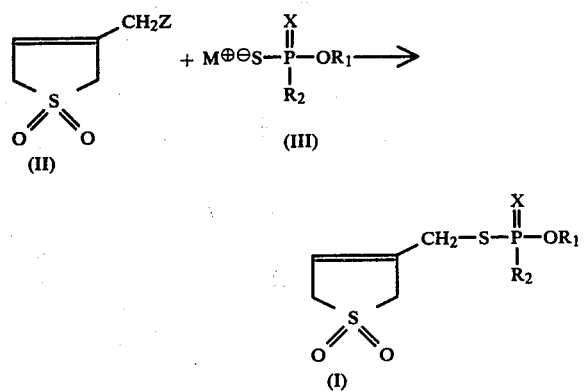

wherein X, $R_1$ and $R_2$ are as previously defined, Z is halogen and $M^\oplus$ is a Group IA metal cation or ammonium.

Reaction (1) is carried out by mixing II and III together in an inert organic solvent, followed by stirring the mixture for about 16 to 20 hours. For convenience, the reaction may be carried out at ambient temperature and pressure. An aliquot of water is then added and the product purified by conventional procedures such as washing, extraction and chromatography. Preferred inert organic solvents include acetone and acetonitrile, other suitable solvents include methylethyl ketone, ether, benzene, dimethoxyethane and other similar inert organic solvents.

The phosphorus reagent (III) where $R_1$ is alkyl and $R_2$ is alkoxy is commercially available.

The phosphorus reagent (III) where $R_2$ is lower alkyl, lower alkylthio or phenyl may be prepared according to the following reaction scheme:

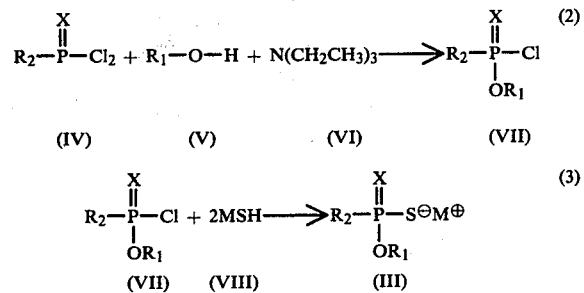

wherein X, $R_1$ and M are as defined in conjunction with Formula I and reaction (1).

Reaction (2) is carried out by adding an approximately equimolar amount of (V) to a stirred solution of (IV) in benzene. An approximately equimolar amount of (VI) is slowly added in a dropwise manner over a period of from about 0.5 to 1 hour. After the addition was complete, the reaction mixture was stirred for an extended period of time, about 16 hours, filtered and the solvent stripped. Other inert solvents such as ether may be used in place of benzene.

The MSH (VIII) used in reaction (3) is prepared in situ by dissolving MOH in isopropyl alcohol by stirring, followed by a period of additional stirring from about 2 to 4 hours. Hydrogen sulfide gas was added by bubbling it through the MOH-alcohol mixture. The resulting mixture was then stirred for about 2-4 hours to give the (VIII) as a solution or slurry.

Reaction (3) is carried out by adding product (VII) of reaction (2) to mixture (VIII) in a ratio of about two equivalents (VIII) per equivalent of (VII) in several portions. The reaction mixture is stirred for an extended period of time, about 5 to about 12 hours and then refluxed for about 1 to about 3 hours. The solvent is stripped and chased using benzene. The product (III) is washed with hexane and ethyl ether.

The phosphorus reagent (III) where $R_2$ is the group $-NR_3R_4$ may be prepared according to the following reaction scheme:

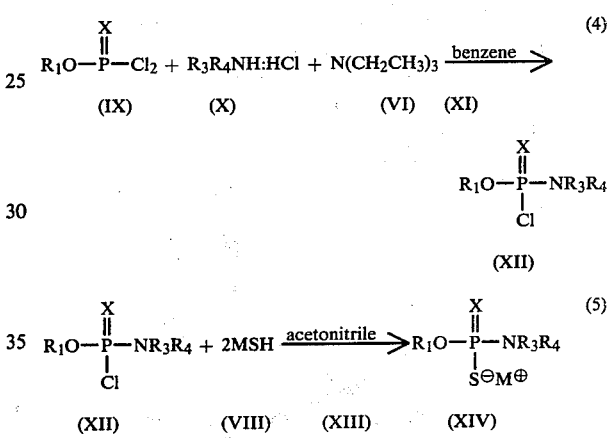

wherein X $R_1$, $R_3$, $R_4$ and M are as defined in conjunction with Formula (I) and reaction (1).

Reaction (4) is carried out by the addition of (VI) to a stirred mixture of (IX) and (X) in (XI). It is preferred that the addition be made slowly, preferably in a dropwise manner. Since the reaction is exothermic, it is preferred that the reaction vessel be cooled during the addition by means such as by use of an ice water bath. Once the reaction is complete, the solvent (XI) is stripped. The crude product (XII) may then be purified by conventional procedures such as washing extraction, and fast chromatography. Aside from benzene, other suitable solvents include benzene isopropyl alcohol, ethyl ether, dioxane, and other inert organic solvents.

The MSH used in reaction (5) is a commercially available hydrosulfide hydrate. Alternatively, MSH may be prepared in situ by the procedure described in connection with reaction (3).

Reaction (5) is carried out by adding (VIII) to a mixture of (XII) in (XIII). Preferably, the addition is done well at once. The resulting mixture is then refluxed for an extended period of time, for about 2 days. After the solvent (XIII) is stripped, the crude product may be purified by conventional means such as extraction and washing.

The 3-halomethyl-3-sulfolene intermediate (II) is prepared by reacting the corresponding 3-methyl-3-sulfolene compound with a selective halogenating agent.

Suitable selective halogenating agents include N-bromosuccinimide and sulfuryl chloride.

For example, the 3-halomethyl-3-sulfolene intermediate (II) where Z is bromo used in the preparation of the compounds of Formula I is prepared by selective bromination of 3-methyl-3-sulfolene with N-bromosuccinimide according to the following reaction scheme:

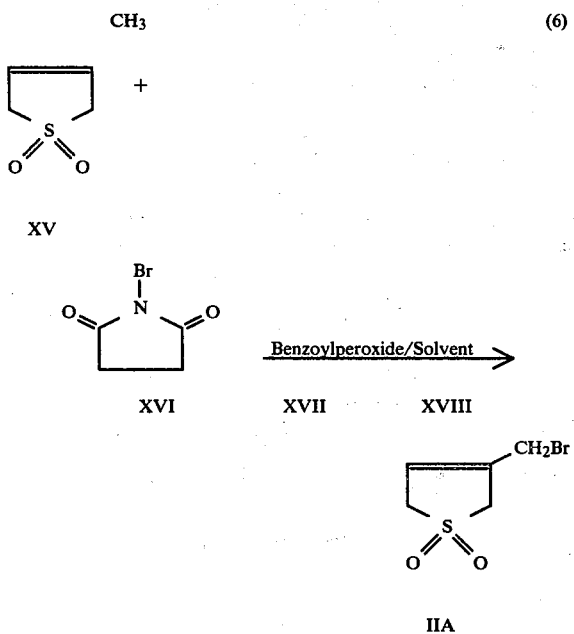

Reaction (6) is carried out by combining XV, XVI, XVIII and a catalytic amount of XVII. The resulting mixture is heated to reflux and then refluxed for about 4 to 20 hours. The reaction mixture is cooled and the product IIA may be isolated by conventional procedures such as filtration, stripping, chromatography, crystallization and the like.

The compounds of this invention are useful for controlling fungi, particularly plant fungal infections and late blights, including those listed in Table II. However, some fungicidal compounds of this invention may be more fungicidally active than others against a particular fungi. Additionally, some of the compounds of this invention show insecticidal activity.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

When used as insecticides, the compounds can be stored and applied as formulations incorporated with compatible biologically inert extenders or carriers such as are typically employed for faciliating dispersion of active ingredients for agricultural chemical applications. These formulations typically contain about from 0.5 to 95 weight % of the present compound, and optionally can contain compatible insecticides, fungicides, etc., and the remainder biologically inert material including dispersing agents, emulsifying agents, wetting agents and carriers.

Such insecticidal formulations can be formulated as sprays, dusts, or granules and applied to the insects and/or their environment or hosts susceptible to insect attack. They can be formulated as granules of large particle size, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5% to 80% active ingredient (pesticide), and the rest inert material, which includes dispersing agents, emulsifying agents and wetting agents. The powder may be applied to the soil as a dry dust, or preferably as a suspension in water. Typical carriers include Fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the pesticidal composition.

Dusts are freely flowing admixtures of the active ingredient with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about fifty microns. A typical dust formulation useful herein contains about 65–80 weight % silica and 35–20 weight % of the compound(s) of the invention.

Useful liquid concentrates include the emulsifiable concentrates, which are homogeneous liquid or paste compositions which are readily dispersed in water or other dispersant, and can consist entirely of the compound(s) of the invention with a liquid or solid emulsifying agent, or can also contain a liquid carrier, such as xylene, heavy aromatic naphthas, isophorone, and other non-volatile organic solvents. These concentrates are usually dispersed in water, or their liquid carrier, and then applied as a spray or paint to the area to be treated.

Other useful formulations include simple solutions of the active compound in a dispersant in which it is completely soluble at the desired concentration, such as acetone, alkylated naphthalenes, xylenes, or other organic solvents. These concentrates are usually dispersed in water, or their liquid carrier, and then applied as a spray or paint to the area to be treated.

Granular formulations, wherein the pesticide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying pesticides are well known in the art.

In fungicidal compositions, the percentages by weight of the active compound may vary according to the manner in which the composition is to be applied and the particular type of formulation, but in general comprise 0.5% to 95% of the toxicant by weight of the fungicidal composition.

Optimum insecticidal formulation concentrations and the manner and frequency of application may vary somewhat with the particular species of insect, the degree of infestation, the environment, including type of soil, soil conditions and weather conditions (e.g., rain fall), and can be obtained by routine experimentation.

The compounds of this invention may be formulated and applied with other active ingredients, including other compatible insecticides, fungicides, nematocides, bacteriocides, anti-viral agents, herbicides, plant-growth regulators, fertilizers, etc.

A further understanding of my invention can be had from the following non-limiting examples.

EXAMPLE 1

Preparation of 3-(Bromomethyl)-3-sulfolene

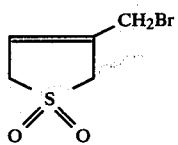

In a reaction vessel, 21.0 gms (0.1591 moles) 3-methyl sulfolene, 28.32 gms (0.1591 moles) N-bromo succinimide, 1.9 gms (0.0008 moles) benzoyl peroxide and 250 ml chlorform were combined. The resulting mixture was heated to reflux and then refluxed for 20 hours. The reaction mixture was cooled to 0° C. and then filtered to remove the succinimide. The filtrate was stripped until only a small amount of solvent remained. The remaining solids were removed by filtration, and the remainder of the solvent was stripped to give an orange oil. Ether was added to the oil. After a few minutes, the solids crystallized. Filtration and drying yielded 11.5 gms of the product. The NMR and IR spectra confirmed the structure.

EXAMPLE 2

Preparation of O,O-Diethyl-S-(3-sulfolenylmethyl) phosphonodithioate

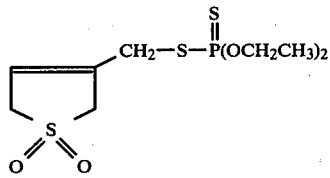

To a solution of 4.3 g (0.0203 moles) of the product of Example 1 dissolved in 75 ml acetonitrile, 4.1 g (0.0203 moles) of

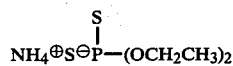

(ammonium O,O diethylphosphorodithioate) was added in one portion. The resulting mixture was then allowed to stir at room temperature overnight. Immediately after the addition, a lot of ammonium bromide salts precipitated.

The next day, the reaction mixture was poured into water (about 75 ml), and then extracted with methylene chloride (about 75 ml). The methylene chloride phase was dried over magnesium sulfate and the solvent stripped. The resulting oil was chromatographed on a 10-inch silica gel column, eluting first with methylene chloride followed by 10% acetone methylene chloride to give 3.3 g of the product, a yellow oil.

Elemental analysis for $C_9H_{17}O_4PS_3$ showed: calculated % C 34.16, % H 5.42, and % NO; found % C 35.24, % H 5.52 and % N 0.34.

EXAMPLE 3

Preparation of Ethyl-O-ethylphosphonothioic chloride

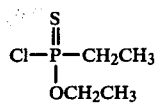

To a mixture of 163.0 gms (1.0 mole)

(ethylphosphonothioic dichloride) dissolved in 500 ml benzene, 46.0 gms (1.0 mole) ethanol was added. To the resulting mixture, 101.0 gms (1.0 mole) triethylamine was added dropwise, over a period of 30 minutes. The addition was slightly exothermic. The reaction mixture was then allowed to stir overnight. The solids were filtered and the solvent was stripped to give 158.0 gms of the product, a light yellow oil.

EXAMPLE 4

Preparation of Potassium ethyl-O-ethylphosphorodithioate

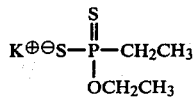

To a stirred mixture of 104.3 gms (1.86 moles) potassium hydroxide in 500 ml isopropyl alcohol, 75.8 gms (1.86 moles+20% excess) hydrogen sulfide gas was introduced over a period of about 30 minutes. The resulting mixture was allowed to stand overnight. Then, to that mixture, 160 gms (0.927 moles) of the product of Example 3 was added slowly, with some exotherm during the addition. After the addition, a lot of salt (KCl) separated. The reaction mixture was stirred at room temperature for a couple of hours, and then heated to reflux and refluxed one hour. The mixture was cooled to room temperature. The mixture was filtered to remove insoluble material and the filtrate stripped. Ether was added to the residue from stripping, the mixture stirred and then filtered. Air drying of the solids on filter paper, gave the product.

EXAMPLE 5

Preparation of Ethyl-O-ethyl-S-(3-sulfolenylmethyl)phosphonodithioate

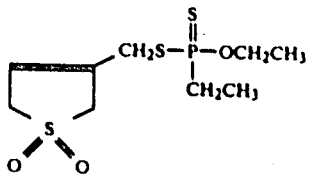

To a solution of 6.33 gms (0.03 moles) of the product of Example 1 in 50 ml acetonitrile, 6.24 gms (0.03 moles) of the product of Example 4 was added in one portion. The resulting mixture was allowed to stir at room temperature overnight.

The reaction mixture was added to water (about 200 ml) and extracted with methylene chloride. The organic phase was separated and dried over magnesium sulfate. The solvent was stripped and the residue was chromatographed on silica eluting with 25% acetone in methylene chloride to give 4.2 gms of product, a yellow oil.

Elemental analysis for $C_9H_{17}O_3PS_3$ showed: calculated % C 35.98, % H 5.71; and % N 0.00; found % C 37.96, % H 6.24, and % N 0.23.

EXAMPLE 6

Preparation of Ethyl-O-ethyl-S-(3-sulfolenylmethyl) phosphinothioate

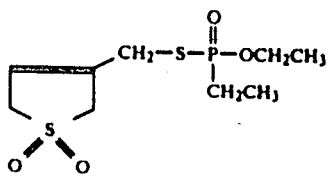

After dissolving 4.3 g (0.0203 moles) of the product of Example 1 in 75 ml acetonitrile, 3.6 gms (0.203 moles) of S-sodio-(ethyl-O-ethylphosphinothioate)

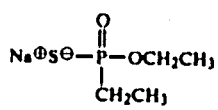

The resulting mixture was stirred overnight at room temperature.

The next day, the reaction mixture was poured into water (about 75 ml) and then extracted with methylene chloride (about 75 ml). The methylene chloride phase was dried over magnesium sulfate and the solvent stripped. Column chromatography over silica eluting with 25% acetone in methylene chloride gave 2.5 g of the product, a yellow oil.

Elemental analysis for $C_9H_{17}O_4PS_2$ showed: calculated % C 38.01, % H 6.03, and % N 0; found % C 38.93, % H 5.97, and % N 0.05.

EXAMPLE 7

Preparation of

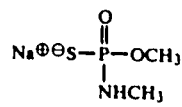

(A) A mixture of 80.0 gms (0.5 moles) dimethylchlorothio-phosphate

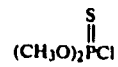

and 200 ml methylene chloride was cooled to 0° in an ice bath. To that cooled solution, 52.5 gms (1.5 moles) ammonium hydroxide was added slowly. The resulting mixture was allowed to stir overnight at room temperature. The layers were separated. The methylene chloride layer was dried over magnesium sulfate. Stripping of the methylene chloride gave a quantitative yield of

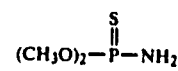

(B) Over a period of thirty minutes, 11.5 gms (0.5 mole) of sodium was allowed to dissolve in 30 ml methanol; during that time the temperature of the mixture was allowed to increase to 40° C. The mixture was then stirred for 30 minutes. To the mixture, 45 gms (0.5 mole) N-butyl mercaptan was slowly added and the resulting mixture was stirred for an hour. To that mixture, 70 gms (0.5 mole) of the product of Step (A),

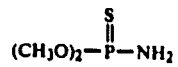

was added with a very slight exotherm. The reaction mixture was then refluxed for two hours and then stirred overnight at room temperature.

The reaction mixture was filtered to remove insoluble matter and the murky filtrate stripped. Ether was added to the residue. The ether mixture was filtered to remove the solid product which was dried at room temperature. The NMR spectrum confirmed the structure.

EXAMPLE 8

Preparation of O-Methyl-S-(3-Sulfolenyl-methyl) phosphoroamidothioate

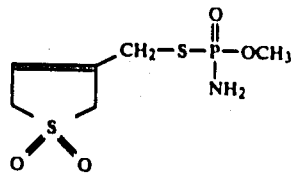

To a mixture of 10.0 gms (0.051 moles) of the product of Example 1 dissolved in 75 ml acetone, 8.2 gms (0.55 moles) of the product of Example 7 was added in one portion. The resulting mixture was heated to reflux and refluxed for 2 hours. The reaction was then allowed to cool to room temperature over an hour. The mixture was filtered to remove salts; the filtrate was then stripped. The residue was chromatographed on a silica column eluting with pure acetone to give 3.6 gms of the product, a white solid with melting point 139°–141° C.

Elemental analysis for $C_{16}H_{12}NO_4PS_2$ showed: calculated % C 28.01, % H 4.70, and % N 5.44; found % C 29.58, % H 4.99, and % N 5.86.

EXAMPLE 9

Preparation of O,N-dimethyl-S-(3-sulfolenylmethyl) phosphoroamidothioate

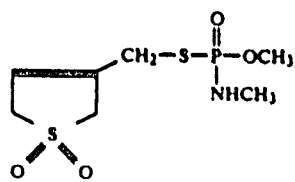

To 6.33 g (0.03 moles) of the product of Example 1 in 75 ml acetone, 4.9 g (0.03 moles) of S-sodio-O,N-dimethylphosphoroamidothioate

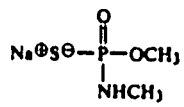

was added in one portion.

The reaction mixture was then heated to reflux and refluxed for 4 hours. Thin layer chromatography of the reaction mixture confirmed formation of the product. The reaction mixture was filtered to remove solids, and the filtrate was stripped to give a residue, the crude product. Methylene chloride (about 5 ml) was added to the residue and the resulting mixture chromatographed eluting with pure acetone to give 37 gms of the product, a white solid with a melting point of 85°–86° C.

Elemental analysis for $C_7H_{14}NO_4PS_2$ showed: calculated % C 30.99, % H 5.20, and % N 5.16; found % C 31.99, % H 5.64, and % N 5.41.

Compounds made in a manner consistent with Examples 1 to 9 are found in Table I.

EXAMPLE A

Grape Downy Mildew Control

The compounds of the invention were tested for the control of the Grape Downy Mildew organism *Plasmopara viticola*. Detached leaves, between 70 and 85 mm in diameter, of 7-week-old *Vitis vinifera* grape seedlings (cultivar Emperor) were used as hosts. The leaves were sprayed with a solution of the test compound in acetone. The sprayed leaves were dried, inoculated with a spore suspension of the organism, placed in a humid environmental chamber and incubated at 66° F. to 68° F. and about 100% relative humidity. After incubation for 2 days, the plants were then held in a greenhouse 7 to 9 days; then the amount of disease control was determined. The percent disease control provided by a given test compound was based on the percent disease reduction relative to untreated check plants. The results are tabulated in Table II.

EXAMPLE B

Tomato Late Blight

Compounds of this invention were tested for the preventive control of the Tomato Late Blight organism *Phytophthora infestans*. Five- to six-week-old tomato seedlings (cultivar Bonny Best) were used. The tomato plants were sprayed with a 250 ppm suspension of the test compound in acetone, water and a small amount of a non-ionic emulsifier. The sprayed plants were then inoculated 1 day later with the organism placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II.

EXAMPLE C

Celery Late Blight

The Celery Late Blight tests were conducted using celery plants (Utah) 11 weeks old. The Celery Late Blight organism was *Septoria apii*. The celery plants were sprayed with solutions of the candidate toxicant (test compound) mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given candidate toxicant (test compound) is based on the percent disease reduction relative to untreated check plants. The results are reported in Table II.

EXAMPLE D

Tomato Early Blight

Compounds of this invention were tested for the control of the Tomato Early Blight organism *Alternaria solani conida*. Tomato seedlings (variety Bonny Best) of 6 to 7 weeks old were used. The tomato plants were sprayed with a 250 ppm solution of the test compound in an acetone-and-water solution containing a small amount of nonionic emulsifier. The sprayed plants were inoculated 1 day later with the organism, placed in an environmental chamber and incubated at 66° F. to 68° F. and 100% relative humidity for 24 hours. Following the incubation, the plants were maintained in a greenhouse for about 12 days. Percent disease control provided by a given test compound was based on a comparison to the percent disease development on untreated check plants. The compounds tested and the results are tabulated in Table II.

EXAMPLE E

Bean Rust Eradication

Compounds of this invention were tested for the eradication of Bean Rust, using 16 to 19 day old pinto bean plants. The pinto bean plants were inoculated with *Uromyces phaseoli typica* in an environmental chamber set for 100% relative humidity and 20°–21° C. After the Bean Rust has developed, one half of the plants are sprayed with solutions of the test compound in acetone. The percent disease control is determined based on the percent disease control reduction in the plants treated with test solution relative to the untreated plants. The results are tabulated in Table II.

EXAMPLE F

Bean Powdery Mildew

The compounds of the invention were tested for control of the Bean Powdery Mildew organism *Erisiphe polygoni*. Seedling bean plants were sprayed with a 250 ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to untreated check plants. The results are tabulated in Table II.

EXAMPLE G

Aphid Control

Compounds of this invention were tested for their insecticidal activity against cotton aphids (*Aphis gossypii* Glover). An acetone solution of the test compound containing a small amount of non-ionic emulsifier was diluted with water to give a concentration of 40 ppm. Cucumber leaves infested with cotton aphids were dipped in the test compound solution. Mortality readings were taken after 24 hours. The results expressed as % control, are tabulated in Table III.

EXAMPLE H—APHID SYSTEMIC EVALUATION

This procedure is used to assess the ability of a candidate insecticide to be absorbed through the plant root system and translocate to the foliage.

Two cucumber plants planted in a 4-inch fiber pot with a soil surface area of 80 cm² are used. Forty ml of an 80 ppm solution of the candidate insecticide is poured around the plants in each pot. (This corresponds to 40 g/cm² of actual toxicant). The plants are maintained throughout in a greenhouse at 75° to 85° F. 48 hours after the drenching, the treated plants are infested with aphids by placing well colonized leaves over the treated leaves so as to allow the aphids to migrate easily from the treated leaf. Three days after infestation, mortality readings were taken. The results are tabulated in Table III in terms of percent control.

EXAMPLE I

Housefly

Compounds of this invention were tested for their insecticidal activity against the housefly (*Musca domestica* L.). A 500-ppm acetone solution of the test compound was placed in a microsprayer (atomizer). A random mixture of anesthetized male and female flies was placed in a container and 55 mg of the above-described acetone solution was sprayed on them. A lid was placed on the container. A mortality reading was then taken after 24 hours. The results are expressed as % control and are reported in Table III.

EXAMPLE J

American Cockroach

Compounds of this invention were tested for their insecticidal activity against the American cockroach (*Periplaneta americana* L.). A 500-ppm acetone solution of the test compound was placed in a microsprayer (atomizer). A random mixture of anesthetized male and female roaches was placed in a container and 55 mg of the above-described solution was sprayed on them. A lid was placed on the container. A mortality reading was made after 24 hours. The results, expressed as % control, are reported in Table III.

EXAMPLE K

Alfalfa Weevil

Compounds of this invention were tested for their insecticidal activity against the alfalfa weevil (*H. brunneipennis Boheman*). A 500-ppm acetone solution of the test compound was placed in a microsprayer (atomizer). A random mixture of male and female weevils was placed in a container and 55 mg of the above-described acetone solution was sprayed on them. A lid was placed on the container. A mortality reading was made after 24 hours. The results are expressed as % control and are tabulated in Table III.

EXAMPLE L

Rootworm Control

The compounds of the invention were tested for control of Corn Rootworm (*Diabrotica undecimpunctata u*). A batch of 20 to 30 two-day old Diabrotica eggs was placed on the bottom of a 237 cc clear plastic cup. These eggs were then covered with about 45 cc of soil containing 15 ppm of the test compound. The soil is watered with 15 cc of water. The corn seeds, presoaked for 2 hours, were evenly distributed on the soil surface. Then an additional 45 cc of the same treated soil was added to cover the seeds, and this soil was watered with an additional 15 cc of water. The test cup was kept at 70° F. with occasional light watering just to keep the soil damp. For 14 to 16 days, the test unit was examined under a dissecting microscope, by observing the corn roots and larvae through the cup's clear plastic walls. Control of newly hatched larvae was rated by visually evaluating the degree of corn root damage by feeding larvae in conjunction with the physical presence of live and/or dead larvae. The results are tabulated in Table III.

EXAMPLE M

Cabbage Looper

Compounds of this invention were tested for their insecticidal activity against cabbage looper (*Trichoplusia ni*). An acetone solution of the test compound containing a small amount of non-ionic emulsifier was diluted with water to give a concentration of 500 ppm. Excised cucumber leaves were dipped in the test compound solution and allowed to dry. The leaves were then infested with cabbage looper larvae. Mortality readings were taken after 24 hours. The results are expressed as % control and are reported in Table III.

EXAMPLE N

Control of Mosquito Larvae

The compounds of this invention were tested for control of mosquito larvae (*Aedes aegypti*). A plastic cup was filled with 90 ml deionized water and then infested with early 4th-stage mosquito larvae contained in 10 ml water. One rabbit food pellet was added to the cup to provide food for the larvae. A 200-microliter aliquot of 500-ppm solution of the test compound was added to the cup. The water was then thoroughly mixed to give a final concentration of test compound of 0.1 ppm. The cup was covered with a plastic lid in order to prevent evaporation and to confine any subsequently emerging adult mosquitos. The cup was kept at 27° C. for 6 days at which time mortality readings were taken. The results, expressed as % control, are reported in Table III.

TABLE II

| Compound Number | Fungicidal Activity | | | | | |
|---|---|---|---|---|---|---|
| | Grape Downy Mildew | Tomato Late Blight | Celery Late Blight | Tomato Early Blight | Bean Rust Eradication | Bean Powdery Mildew |
| 1 34054 | 14 | 0 | 0 | 50 | 14 | 0 |
| 2 34643 | 98 | 0 | 39 | 68 | 6 | 0 |
| 3 34163 | 0 | 0 | 0 | — | 13 | 0 |
| 4 34646 | 0 | 0 | 56 | — | 0 | 0 |
| 5 34647 | 0 | 35 | 0 | — | 13 | 0 |
| 6 34951 | 18 | 0 | — | 0 | 0 | 11 |
| 7 34644 | 81 | 35 | 39 | — | 0 | 0 |
| 8 34057 | 0 | 0 | 0 | 50 | 0 | 0 |
| 9 34950 | 0 | 0 | — | 0 | 0 | 0 |

TABLE III

| Compound Number | Insecticidal Activity | | | | | | | | |
|---|---|---|---|---|---|---|---|---|---|
| | Aphid | Aphid Sys | Housefly | Am. Roach | Alf. Weevil | Rootworm | Cab. Looper | Pupa | Mos. Larva |
| 1 34054 | 75 | 0 | 0 | 0 | 0 | — | 0 | 0 | — |
| 2 34643 | 98 | 0 | 0 | 100 | 20 | 100 | 30 | 0 | 90 |
| 3 34163 | 100 | 10 | 90 | 100 | 40 | — | 0 | 0 | 70 |
| 4 34646 | 96 | 100 | 0 | 78 | 20 | 0 | 0 | 0 | 0 |
| 5 34647 | 99 | 85 | 99 | 99 | 20 | 0 | 0 | 0 | 100 |
| 6 34951 | 99 | 99 | 90 | 94 | 0 | 0 | 30 | 0 | 0 |
| 7 34644 | 0 | 0 | 0 | 50 | 0 | 0 | 0 | 0 | 0 |
| 8 34057 | 0 | 0 | 0 | 0 | 0 | — | 0 | 0 | 0 |
| 9 34950 | 0 | 0 | 0 | 0 | 0 | 0 | 0 | 0 | 0 |

What is claimed is:

1. A compound of the formula:

TABLE I

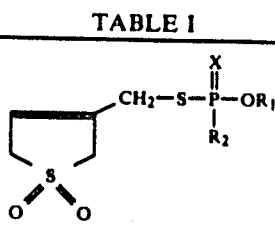

| Compound # | X | $R_1$ | $R_2$ | Physical State | % Carbon | | % Hydrogen | | % Nitrogen | |
|---|---|---|---|---|---|---|---|---|---|---|
| | | | | | Calc. | Found | Calc. | Found | Calc. | Found |
| 1 34054 | S | —$CH_2CH_3$ | —$OCH_2CH_3$ | Yellow oil | 34.16 | 35.28 | 5.42 | 5.52 | 0 | 0.34 |
| 2 34643 | S | —$CH_2CH_3$ | —$CH_2CH_3$ | Yellow oil | 35.98 | 37.96 | 5.71 | 6.24 | 0 | 0.23 |
| 3 34163 | O | —$CH_2CH_3$ | —$CH_2CH_3$ | Yellow oil | 38.01 | 38.93 | 6.03 | 5.97 | 0 | 0.05 |
| 4 34646 | O | —$CH_3$ | —$NHCH_3$ | White solid, mp 85–86° C. | 30.99 | 31.99 | 5.20 | 5.64 | 5.16 | 5.41 |
| 5 34647 | O | —$CH_3$ | —$NH_2$ | White solid, mp 139–141° C. | 28.01 | 29.58 | 4.70 | 4.99 | 5.44 | 5.86 |
| 6 34951 | O | —$CH_2CH_3$ | —$NH_2$ | Tan solid, mp 113–117° C. | 30.99 | 31.85 | 5.2 | 5.14 | 5.16 | 4.86 |
| 7 34644 | O | —$CH_2CH_3$ | —$SCH_3$ | Yellow Oil | 31.77 | 32.27 | 5.00 | 5.12 | 0 | 0.06 |
| 8 34057 | S | —$CH_2CH_3$ | phenyl | Yellow Oil | 44.81 | 45.2 | 4.92 | 5.09 | 0 | 0.2 |
| 9 34950 | O | —$CH_2CH_3$ | phenyl | Yellow Oil | 46.97 | 46.51 | 5.16 | 5.27 | 0 | 0.46 |

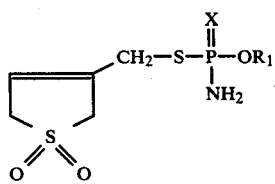

wherein X is sulfur or oxygen; and $R_1$ is lower alkyl.

2. A compound according to claim 1 wherein X is oxygen and $R_1$ is methyl.

3. A compound according to claim 1 wherein X is oxygen and $R_1$ is ethyl.

4. An insecticidal composition comprising a biologically inert carrier and an insecticidally effective amount of a compound of claim 1.

5. An insecticidal composition comprising a biologically inert carrier and an insecticidally effective amount of a compound of claim 2.

6. An insecticidal composition comprising a biologically inert carrier and an insecticidally effective amount of a compound of claim 3.

7. A method of killing insects which comprises contacting said insect or its environment with an insecticidally effective amount of a compound of claim 1.

8. A method of killing insects which comprises contacting said insect or its environment with an insecticidally effective amount of a compound of claim 2.

9. A method of killing insects which comprises contacting said insect or its environment with an insecticidally effective amount of a compound of claim 3.

* * * * *